United States Patent [19]

Oka et al.

[11] Patent Number: 5,169,521
[45] Date of Patent: Dec. 8, 1992

[54] APPARATUS FOR COUNTERCURRENT CHROMATOGRAPHY SEPARATIONS

[75] Inventors: Hisao Oka, Nagoya, Japan; Yoichiro Ito, Bethesda, Md.

[73] Assignee: The United States of America as represented by the Department of Health and Human Services, Washington, D.C.

[21] Appl. No.: 798,328

[22] Filed: Nov. 26, 1991

Related U.S. Application Data

[63] Continuation-in-part of Ser. No. 450,111, Dec. 13, 1989, abandoned.

[51] Int. Cl.$^5$ .............................................. B01D 15/08
[52] U.S. Cl. .................... 210/198.2; 210/85; 210/90; 210/137; 210/149; 210/181; 210/657
[58] Field of Search ............. 210/656, 657, 96.1, 210/85, 90, 137, 149, 181, 198.2; 73/61.1 C; 422/70

[56] References Cited

U.S. PATENT DOCUMENTS

| | | | |
|---|---|---|---|
| 4,019,372 | 4/1977 | Parkett et al. | 210/198.2 |
| 4,051,025 | 9/1977 | Ito | 210/198.2 |
| 4,116,046 | 9/1978 | Stein | 210/198.2 |
| 4,137,161 | 1/1979 | Shimada et al. | 210/198.2 |
| 4,312,835 | 1/1982 | Zoltan et al. | 73/61.1 C |
| 4,404,845 | 9/1983 | Schrenker | 73/61.10 |
| 4,484,061 | 11/1984 | Zelinka et al. | 210/198.2 |
| 4,487,693 | 12/1984 | Ito | 210/198.2 |
| 4,814,089 | 3/1989 | Kumar | 436/161 |

OTHER PUBLICATIONS

Y. Ito, et al, *Crit. Rev. Anal. Chem.* "High Speed CCC" 17(1) pp. 65–143 (1986).
Y. Ito, et al, *J. Chromatogr.*, 244 "High Speed Preparative CCC" pp. 247–258 Jul. 1982.
T. Y. Zhang, et al, *J. Chromatogr.*, 435 "Separation of Flavonoids" pp. 159–166 Jan. 1988.
T. Y. Zhang, et al, *Liq. Chromatogr.* 11(1) "Separation of Flavonoids", pp. 233–244 (1988).

*Primary Examiner*—Ernest G. Therkorn
*Attorney, Agent, or Firm*—Lowe, Price, LeBlanc & Becker

[57] ABSTRACT

The invention relates to an improved continuous countercurrent chromatography apparatus. The invention further relates to an improved method of countercurrent chromatography comprises filling a separation column with a first solvent, introducing into the column a sample solute to be separated, continuously pumping a second solvent into the column, the second solvent being substantially immiscible with the first solvent, maintaining the solvent flowing out of the column at a temperature effective to avoid clouding thereof, spectrophotometrically monitoring the temperature-maintained separating fractions flowing out of the column, and applying back-pressure to the solvent flowing into and out of the monitor.

5 Claims, 8 Drawing Sheets

APPARATUS FOR COUNTERCURRENT CHROMATOGRAPHY SEPARATIONS

This application is a continuation-in-part of application Ser. No. 07/450,111 filed Dec. 13, 1989, now abandoned.

TECHNICAL FIELD

This invention relates to a countercurrent chromatography apparatus and to a method of monitoring its effluent. More particularly, this invention provides an improvement to known countercurrent chromatography apparatus technology which substantially avoids the development of turbidity in the flow cell as well as the production of bubbles which interfere with the production of substantially noiseless tracings and improved separation of chemicals.

BACKGROUND ART

High-speed countercurrent chromatography (HSCCC) using a multilayer coiled column is a unique liquid-liquid partition technique that does not require the use of solid supports (Y. Ito, et al *Crit. Rev. Anal. Chem.*, 17 65 (1986)). The use of two immiscible solvent phases in an open column free of solid support matrix can eliminate complications associated with conventional liquid chromatography such as tailing of solute peaks, adsorptive sample loss and deactivation, and sample contamination. On the other hand, counter current chromatography (CCC) separation often encounters difficulties for the stable continuous UV-monitoring of the effluent and, therefore, elution curves must usually be drawn manually by the spectrophotometric analysis of individual fractions after the effluent is fractionated with a fraction collector (Y. Ito, et al, *J. Chromatogr.*, 244 247 (1982); T. Y. Zhang, et al, *J. Chromatogr.*, 435 159 (1988); T. Y. Zhang, et al, *Liq. Chromatogr.*, 11 233 (1988)). In order to avoid the above laborious procedure, it is highly desirous to establish a CCC monitoring system which produces stable UV-tracing of elution curves comparable to those in other chromatographic methods.

U.S. Pat. No. 4,019,372 to Parkell et al shows a liquid chromatography apparatus which uses a flow cell compartment mounted between a light source and a detector. The flow cell is transparent and is encapsulated in a thermally conductive medium for maintaining thermal equilibrium. The connecting tubing is in thermal contact with the flow cell for a sufficient length of time so that any liquid passing through it arrives to thermal equilibrium with the flow cell before entering the optically transparent flow cell. The effluent from the chromatographic column passes through tube which is partially coiled around the flow cell.

U.S. Pat. No. 4,051,025 is one of Dr. Ito's prior patents which is illustrative of an apparatus for which the present invention is intended. This patent shows a helical tube array rotating about its own axis in a gravitational field, where a countercurrent flow is produced by pumping a mobile phase through the rotating end of an helical array filled with a stationary phase. The mobile phase is finally eluted through the tail end of the tube. Any solutes introduced are subjected to a continuous partition process between mobile and stationary phases. At the outlet conduit there is an ultraviolet monitor to analyze the solute fractions. U.S. Pat. No. 4,487,693 is another example of a similar apparatus described by Dr. Ito.

U.S. Pat. No. 4,116,046 is cited to show a chromatography column with a temperature control jacket surrounding the column. This column and jacket are located prior to the detection device. The temperature control device is used to insure proper conditions for reproducible separations. A narrow bore tubing just downstream following the detector is used to establish back pressure and prevent bubbling.

U.S. Pat. No. 4,137,161 describes a liquid chromatographic apparatus having a flow restrictor downstream of the detector unit in order to apply back pressure to a single cell. The flow restrictor consists of a needle valve, a long thin capillary tube and a filter. This design prevents the formation of bubbles in the effluent from the separation column.

U S. Pat. No. 4,312,835 discloses a form of thermally controlling liquid chromatographic samples. The function of a temperature controlled platform is to uniformly maintain solution samples at a predetermined temperature until chromatographic analysis is completed. The patent states that this procedure is especially useful if the sample is labile and degrades at room temperature. The samples are positioned at 3, and the insulating layer is positioned at 2 shown in the figures. The sample holder body is made of a heat conductive material made of an inner surface and an outer surface. Pelteir elements comprise active surface 4*a* and reactive surface 4*b* and sample body surface 1*b* is in intimate contact with Pelteir active surface 4*a*. A heat exchanger is also placed in intimate contact with a Peltier surface 4*b*. Heating and cooling are a function of the active surface of the Peltier element.

U.S. Pat. No. 4,404,845 to Schrenker discloses a heat exchanger for the mobile phase and a separation column in a liquid chromatograph. The patent describes three methods of heat exchange. The third method includes a separation column which is concentrically mounted within a tube through which water flows. Control is maintained by means of a liquid convection thermal regulator. The purpose of temperature control is to avoid temperature gradients in the column and improve consistency of analysis as well as separation. FIG. 1 shows a capillary tube which leads to a heat exchange body. The mobile phase and the sample flow through this body to a separation column located in column compartment. In this patent heating or cooling is attained by heating or cooling the air surrounding the column.

U.S. Pat. No. 4,484,061 is another example of a temperature controlled system for liquid chromatographic columns where a foil-like patterned heating element is wrapped around the chromatographic column. A sensing element is also coextensively mounted with the heating element. The patent states that controlling the temperature of the column dramatically affects peak retention time reproducibility while maintaining a relatively constant base line or background electrical noise level due to solvent flow in the detector.

U.S. Pat. No. 4,814,089 shows the use of tapered restrictors and large interface heating zones for increasing pressure drop. It is also known to use thin walled capillary tubing to facilitate heat transfer. The patent also teaches that the mobile phase should not condense before detection as this would result in ion bursts which would produce extra electronic signals in the detector. While all of the comments in this patent relate to supercritical fluid chromatography and the problems associated with depressurization of the fluid stream, the teachings are not solely limited to this application.

Japanese Patent 1277-056 discloses a cylindrical heater for a chromatographic column arranged between the delivery part and the receiver.

The problems associated with the direct UV-monitoring of the effluent in CCC may be classified into the following four categories.

1) Steady carryover of the stationary phase due to an improper choice of the elution mode and/or the application of an excessively high flow rate of the mobile phase.
2) Migration of the stationary phase into the flow cell which is caused by various conditions such as fluctuation of revolutional speed, vibration of the centrifuge system, and overloading of the sample, which may cause local alteration of the phase volume ratio and the physical properties of the two phases.
3) Turbidity of a thermolabile mobile phase in the flow cell due to altered ambient temperature.
4) Gas bubble formation in the effluent under reduced pressure in the periphery of the flow passage.

Of these, the first two problems may be avoided by choosing appropriate experimental conditions whereas solely a modification of the monitoring system has been found to overcome the latter two problems.

Accordingly, there is a definite need for an improved countercurrent chromatography apparatus which is capable of substantially eliminate turbidity in the flow cell caused by thermolabile components and the formation of gas bubbles in the effluent.

DISCLOSURE OF THE INVENTION

This invention relates to an improved continuous countercurrent chromatography apparatus comprising a separation column provided with first and second ends, feed conduit means for introducing fluids to the first end of the separation column, fluid monitoring means provided with first and second ends, and delivery conduit means connecting the second end of the separation column to the first end of the fluid monitoring means, the improvement comprising a thermal regulator means positioned between the delivery conduit means and the monitoring means, said regulator means being capable of maintaining the fluid entering the monitoring means at a predetermined temperature; and means for applying back-pressure to the fluid exiting the monitoring means, said back-pressure means connected to the second end of the monitoring means.

Also provided herein is a method of countercurrent chromatography comprising filling a separation column with a first solvent;

introducing into the column a sample solute to be separated;

continuously pumping a second solvent into the column, said second solvent being substantially immiscible with the first solvent;

maintaining the solvent flowing out of the column at a temperature effective to avoid clouding thereof;

spectrophotometrically monitoring the temperature-maintained separating fractions flowing out of the column; and applying back-pressure to the solvent flowing out of the monitor to thereby substantially prevent the formation of bubbles in the monitor.

This invention also encompasses a method of improving the monitoring of effluent in continuous countercurrent chromatography, comprising filling a separation column with a first solvent;

introducing into the column a sample solute to be separated;

continuously pumping a second solvent into the column, said second solvent being substantially immiscible with the first solvent;

maintaining the solvent flowing out of the column at a temperature effective to avoid clouding thereof;

spectrophotometrically monitoring the temperature-maintained separating fractions flowing out of the column; and applying back-pressure to the solvent flowing out of the monitor to thereby substantially prevent the formation of bubbles in the monitor.

A more complete appreciation of the invention and many of the attendant advantages thereof will be readily perceived as the same becomes better understood by reference to the following detailed description when considered in connection with the accompanying figures.

Figure 1:
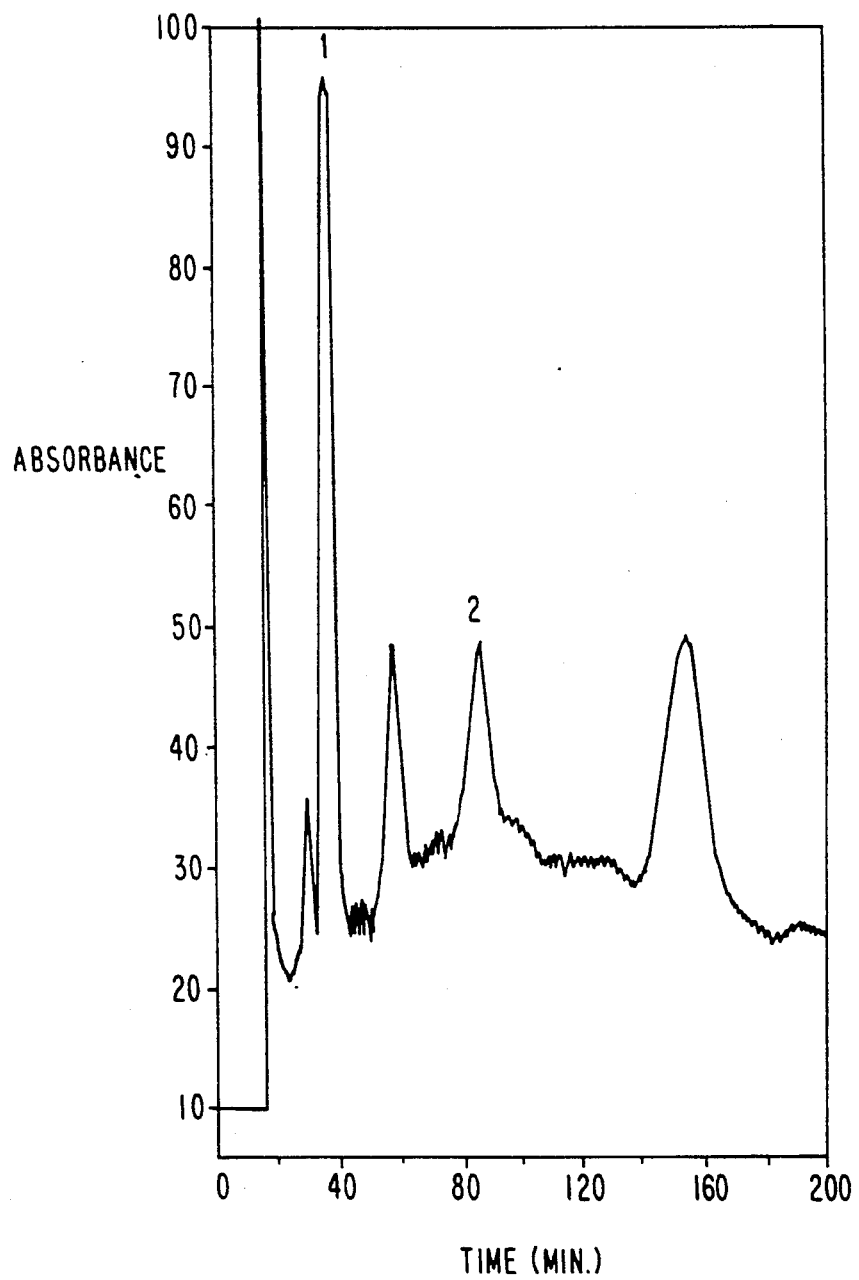
FIG. 1 shows a UV-tracing chart of the separation of flavonoid compounds obtained with a conventional monitoring method for HSCCC obtained in example 7. The experimental conditions were as follows. Monitor: LKB Uvicord S; Flow Cell: Standard type, 3 mm light path, 50 ul capacity; Wavelength: 254 nm; Recorder: Pharmacia Model 482 recorder; Chart Speed: 0.5 mm/min.

Other objects, advantages and features of the present invention will become apparent to those skilled in the art form the following discussion.

BEST MODE FOR CARRYING OUT THE INVENTION

This invention arose from a desire to improve on existing technology relating to continuous countercurrent chromatography. More particularly, the present invention provides a way to overcome the drawbacks encountered by state of the art countercurrent chromatography mostly due to the thermal labile nature of the mobile phase which tends to develop turbidity in the flow cell of the monitor under a slight shift of ambient temperature and to the formation of bubbles which interfere with the monitoring of the effluent of the column.

The inventor has provided an improved apparatus which substantially overcomes these two problems.

It is provided herein an improved continuous countercurrent chromatography apparatus comprising a separation column provided with first and second ends; feed conduit means for introducing fluids to the first end of the separation column; fluid monitoring means provided with first and second ends; and delivery conduit means connecting the second end of the separation column to the first end of the fluid monitoring means, the improvement comprising a thermal regulator means positioned between the delivery conduit means and the monitoring means, said regulator means being capable of maintaining the fluid entering the monitoring means at a predetermined temperature; and means for applying back-pressure to the fluid exiting the monitoring means, said back-pressure means connected to the second end of the monitoring means.

Although the apparatus of the invention can be utilized for the practice of any type of counter-current pressure continuous countercurrent chromatography (HPCCC).

As the main structure for the apparatus any separation column, feed conduit means and spectroscopic monitor may be utilized. Particularly preferred however is an apparatus where the chromatography column is a helical tube and where the column can rotate around its longitudinal axis and the axis can be moved with respect to the horizontal plane to be positioned at an angle thereof. Particularly preferred rotating columns are those where the angle is between about 0° and 90° from the horizontal plane. Preferred conditions relating to the capabilities of the rotation system are those, e.g., described in U.S. Pat. No. 4,051,025 to Ito, the entire content of which is incorporated herein by reference, and particularly the sections relating to the description of the rotational system of the chromatography apparatus.

In a particularly preferred embodiment of the above rotational column, the apparatus has a feed conduit means provided with a sample port and fluid pump means connected to the feed conduit means through the sample port.

In another particularly preferred embodiment, the apparatus further comprises a fraction collector means connected to the outlet of the fluid monitoring means.

Figure 6:
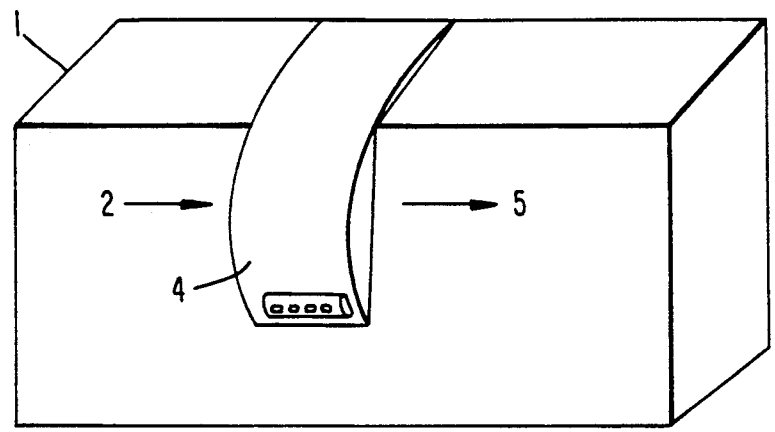
FIG. 6 shows an overall view of a monitor equipped with a flow-cell compartment representing a best mode of the invention.

The spectroscopic monitor (1) will now be described in relation to FIG. 6 accompanying this patent. The light source (2) on the left emits visible or ultraviolet (UV) rays which pass through the flow-cell (3) in the flow-cell compartment (4) and then reach the detector (5) located on the right. The flow-cell compartment (4) may be round in shape so that it can be rotated 180° to adjust the orientation of the flow-cell (3) and thereby meet the choice of the mobile phase as explained below. Unexpectedly improved tracings of the elution curves are obtained with a monitor (1) having this design.

Figure 7:
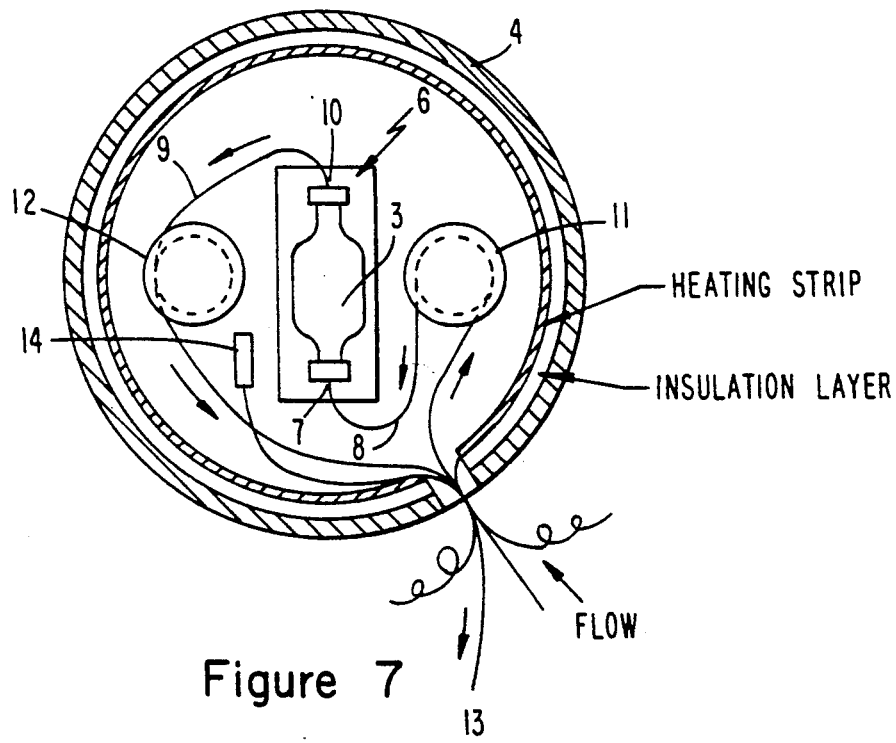
FIG. 7 illustrates the design of a flow-cell compartment representative of a best mode of the invention.

The design of a flow-cell compartment (4) representing a best mode of this invention will now be described in relation to FIG. 7 of this patent. The flow-cell (3) may be mounted at the center of the compartment (4) with a flow-cell support assembly (6) to secure the connections to the flow tube. The inflow flow tube (8) may enter the compartment and form multiple loops around a spool (pre-flow cell spool (11) shown on the right of FIG. 7) before joining the inlet (7) of the flow-cell (3). The outflow flow tube (9) from the outlet (10) of the flow-cell (3) may again form multiple loops around a similar spool (post flow-cell spool (12) shown on the left of FIG. 7) and exits the compartment (4) to deliver the effluent into a fraction collector (13), which is optionally operatively connected to the monitor (1).

The temperature inside the compartment (4) may be regulated by a thermal regulator with a temperature sensor (14) and heating strip which lines the inside of the wall. The orientation of the flow-cell (3) can be adjusted in a manner such that the inlet (7) is positioned at the bottom with a lower phase mobile and the outlet (10) at the top with the upper face mobile. In this manner, the stationary phase is easily eliminated from the flow-cell (3) with the aid of gravity.

The inflow tube loops may serve to equilibrate the temperature of the inflow solvent whereas the outflow loops may provide back-pressure to prevent the formation of gas bubbles in the flow-cell (3) due to sudden pressure drops.

A preferred embodiment of the apparatus is that wherein the separation column is a helical tube and it is rotatably positioned at an angle with the horizontal plane. However, any column chromatography apparatus may be utilized in accordance with the invention as long as it contains the improvements provided herein.

The apparatus of the invention may be utilized for the practice of a method of countercurrent chromatography as taught herein. The method comprises filling a separation column with a first solvent;
introducing into the column a sample solute to be separated;
continuously pumping a second solvent into the column, said second solvent being substantially immiscible with the first solvent;
maintaining the solvent flowing out of the column at a temperature effective to avoid clouding thereof;
spectrophotometrically monitoring the temperature-maintained separating fractions flowing out of the column; and
applying back-pressure to the solvent flowing out of the monitor to thereby substantially prevent the formation of bubbles in the monitor.

The method of the invention is essentially an improvement over prior art methods wherein the conditions, solvents, solvent mixtures and other parameters are selected as an artisan with skill in the art would know.

The present method essentially provides for the practice of countercurrent chromatography whereby in addition to the known steps of filling a separation column, introducing into the column a sample solute to be separated and continuously pumping a second solvent which is substantially immiscible with the first solvent, also provides for maintaining the solvent flowing out of the column at a temperature effective to avoid clouding thereof prior to accessing the spectroscopic monitoring means.

In addition, in order to further improve the spectrophotometrical monitoring of the separating fractions which are maintained at a pre-set temperature, the method provides for the application of back-pressure to the solvent flowing out of the monitor, to thereby substantially prevent the formation of bubbles which may interfere with the monitoring of the sample's content.

Figure 8:
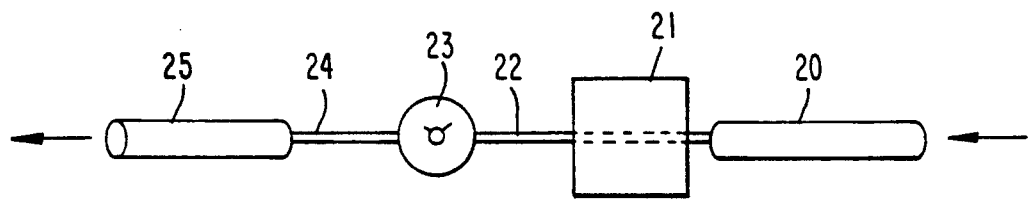
FIG. 8 illustrates a section of the flow line from a preferred embodiment of the present invention; this section has thermal regulating means, a back pressure means, a monitor means, and a signal back pressure means that are representative of a best mode of the invention.

An even more preferred aspect of the invention relating to the flow line in the area of the monitoring means is illustrated by FIG. 8. FIG. 8 shows a preferred arrangement having the flow line (20) leading to the thermal regulator (21), a flow line (22) connected at a first end to the exiting means of the thermal regulator and at a second end to a back pressure means (23) which is inserted between the flow line (22) and the first means of the monitoring means (24) and a second back pressure means (25) connected to the exiting means of the monitoring means (24) at a first end and connected at the second end to the exiting flow line (26). The combination of a first and second back pressure means allows for unexpectedly superior results in both head to tail column and tail to head column arrangements. The unexpected results will be described in more detail below.

Figure 9:
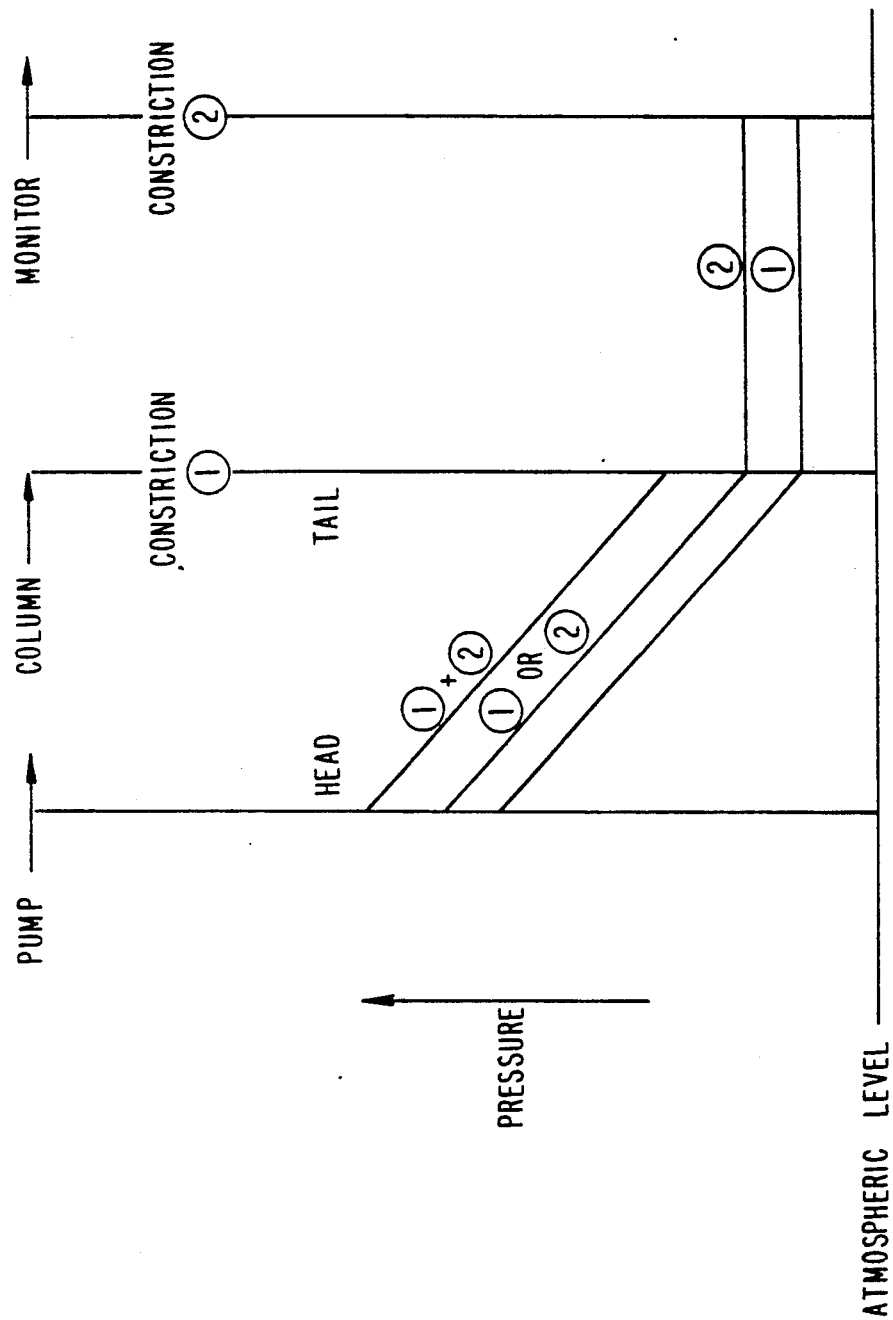
FIG. 9 illustrates a head to tail arrangement for a column and compares system pressure levels for various system arrangements.

FIG. 9 is a chart type arrangement showing the advantages of the present invention in a column head to tail arrangement. In this arrangement a flow line leads from the pump to the head of a column. A flow line then leads from the tail of the column to a monitor and then from the monitor back to the pump. Comparisons of pressure in the system are made when (a) there is no back pressure means (constriction) in the flow line either between the column and the monitor or the monitor and the pump, (b) there is a back pressure means in either the flow line between the tail of the column and the monitor or between the monitor and the pump, or (c) when a back pressure means is inserted between both the tail of the column and the monitor and between the monitor and the pump.

As is clear from the chart in FIG. 9, pressure in the system is above atmospheric pressure without back pressure means and thus does not require a back pressure means for the pump to operate properly. Applicants have discovered that a back pressure means inserted as in situation B (wherein the back pressure means is either in the flow line between the tail of the pump and the monitor or between the monitor and the pump) will allow for higher pressure within the system while helping to control the temperature and pressure within the monitor. Surprisingly, Applicants have discovered that when a back pressure means is inserted both in front of and following the monitor (i.e., a first and second back pressure means are used) that the pressure in the system can be raised even further without damaging the monitor. It is unexpected that putting a back pressure means between the column and the monitor and between the monitor and the pump would allow for a higher pressure within the system and thus provide unexpectedly superior results. below.

Figure 10:
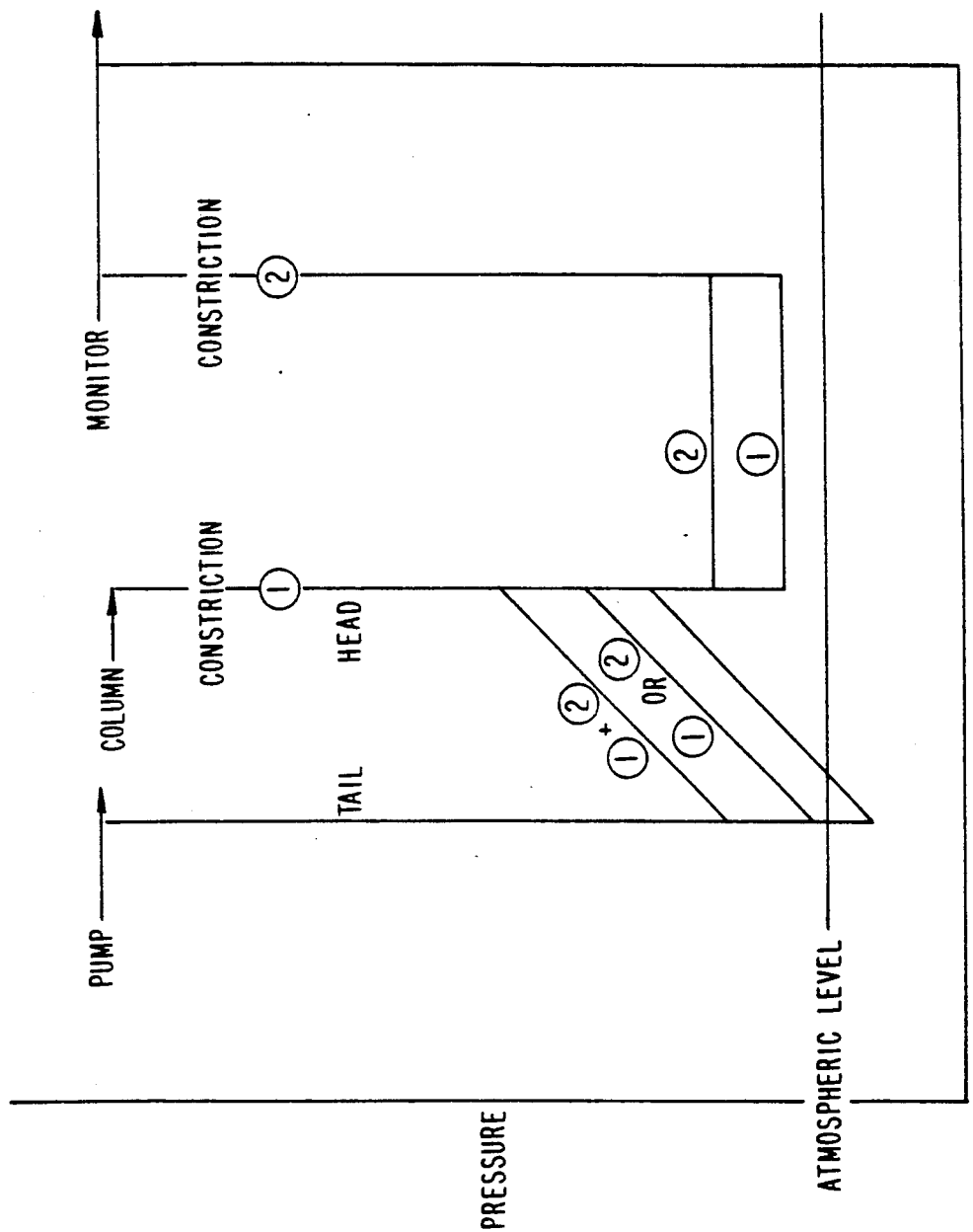
FIG. 10 illustrates tail to head arrangement for a column and compares system pressure levels for various system arrangements.

FIG. 10 is a chart type arrangement showing the advantages of the present invention in a column tail to head arrangement. In this arrangement a flow line leads from the pump to the tail of a column. A flow line then leads from the head of the column to a monitor and then from the monitor back to the pump. Comparisons of pressure in the system are made when (a) there is no back pressure means (constriction) in the flow line either between the column and the monitor or the monitor and the pump, (b) there is a back pressure means in either the flow line between the head of the column and the monitor or between the monitor and the pump, or (c) when a back pressure means is inserted between both the head of the column and the monitor and between the monitor and the pump.

As is clear from the chart in FIG. 10, the pressure in the system is below atmospheric pressure when no back pressure means is used and thus a back pressure means is required for the pump to operate properly and avoid sucking fluid from the reservoir. The chart shows that a back pressure means can be inserted in the flow line either between the head of the column and the pump or between the monitor and the pump in order to raise the pressure in the system to be at least equal to atmospheric pressure and allow for proper operation of the pump and continuous chromatography. However, Applicants have discovered that a back pressure means can be inserted both before and after the monitor to provide a system having two back pressure means which allows for an unexpectedly higher level of pressure in the whole system. It is unexpected that putting a back pressure means between the column and the monitor and between the monitor and the pump would allow for a higher pressure within the system and thus provide unexpectedly superior results.

Applicants have also discovered a system having an unexpected advantage over the prior art. When both a first and second back pressure means are used in the system, the system can advantageously be used for both a head to tail and tail to head arrangement. This is surprisingly unpredictable since one might have suspected that using two back pressure means would have created to high of a pressure within the system for the head to tail arrangement and one of ordinary skill would have not have expected that two back pressure means would have allowed for an even higher pressure in the tail to head column arrangement.

Therefore, it is unexpected for one of ordinary skill in the art that superior results and higher pressures could be obtained in both the head to tail and tail to head arrangement when a back pressure means is inserted both before the monitor and after the monitor in a continuous countercurrent chromatography system.

Also, in a particularly preferred embodiment of the method the column is provided as a helical tube and the method further comprises rotating the column around its longitudinal axis. This method results in the improved separation of a mixture of components as is known in the art. The column's axis is preferably at an angle with a horizontal plane of about 0° to 90°.

Also provided herein is a method of improving the monitoring of effluent in continuous countercurrent chromatography, the method comprising filling a separation column with a first solvent;

introducing into the column a sample solute to be separated;

continuously pumping a second solvent into the column, said second solvent being substantially immiscible with the first solvent;

maintaining the solvent flowing out of the column at a temperature effective to avoid clouding thereof;

spectrophotometrically monitoring the temperature-maintained separating fractions flowing out of the column; and applying back-pressure to the solvent flowing out of the monitor to thereby substantially prevent the formation of bubbles in the monitor.

The conditions for practicing the filling step, the introducing step, the continuous pumping step and the spectrophotometrically monitoring steps are known in the art. By means of example, conditions suitable are described in U.S. Pat. No. 4,051,025 to Ito. However, other conditions may also be utilized.

Conditions for the practice of the rotation of the column around its longitudinal axis are also as described in U.S. Pat. No. 4,051,025 to Ito.

The conditions for maintaining the solvent flowing out of the column at a temperature effective to avoid clouding thereof are as follows. A preferred temperature is that where the solvents and/or solutes added to the solvents remain translucent. An artisan can without undue experimentation take a sample of the solvent and solutes which are to be separated and determine a temperature curve to know what ranges of temperatures will prevent the clouding of the test sample. Some temperatures are provided in the examples but those are solely applicable to the specific cases under experimentation therein.

For practicing the step of applying back-pressure to the solvent flowing out of the monitor, a narrower conduit may be utilized for the effluent exiting the monitor means. This constriction of the diameter of the space accessible to the solvent for flowing out the monitor means will by itself apply back-pressure and slow the flow rate of the solvent out of the monitor means.

Other means to apply back-pressure to the outflowing solvent may also be utilized as are known in the art.

Having now generally described this invention, the same will be better understood by reference to certain specific examples, which are included herein for purposes of illustration only and are not intended to be limiting of the invention or any embodiment thereof, unless so specified.

EXAMPLES

Example 1: Apparatus in Accordance with the Invention

The high-speed countercurrent chromatography apparatus used in this study was a commercially available model of a flow-through coil planet centrifuge called "Ito Multi-layer Coil Separator-Extractor" (P.C. Inc., Potomac, Md.). The column holder is positioned at a distance of 10 cm from the central axis of the centrifuge. The separation column was prepared by winding a long piece of polytetrafluoroethylene (PTFE) tubing, 1.6 mm I.D. and 0.3 mm wall thickness, directly onto the holder hub of 10 cm diameter making multiple coiled layers.

The ratio of the rotational radius to the revolutional radius beta value ranges from 0.5 at the internal terminal to 0.8 at the external terminal. The total capacity of the multilayer coil measures about 280 ml. This apparatus is equipped with an ACCU-FLOpump (Beckman Instruments, Inc., Palo Alto, Calif.) and a speed controller (Bodine Electric Co., Chicago, Ill.). Continuous UV-monitoring was performed with an LKB 2138 Uvicord S UV-monitor (LKB-Produkter AB, Bromma, Sweden) operated at 254 nm and a Pharmacia 482 recorder (Pharmacia, Uppsala, Sweden).

A fine PTFE tube of 0.46 mm I.D. and 3 m in length (Zeus Industrial Products, Raritan, N.J.) was inserted in the flow line between the coiled column and the UV-monitor. The PTFE tube can be heated in a water bath at any desired temperature. A similar tube was applied to the outlet of the UV-monitor to prevent sudden pressure drop which would generate gas bubbles from the mobile phase (See FIGS. 6 and 7 for a preferred embodiment of the apparatus of the invention) (FIG. 8 shows this section of the flow line having a fine tube inserted in the flow line between the column and the U.V. monitor along with the temperature regulating means. For example, temperature is regulated by a water bath and the fine tube is used instead of a larger tube in order that it may also act as a first back pressure means. This first fine tube is attached to the entry means of the monitor and a second fine tube (second back pressure means) is attached to the exit of the monitor at a first end and attached at a second end to the flow line leading back to the pump)..

Example 2: Reagents

Organic solvents including n-hexane, ethly acetate, chloroform, n-butanol, sec.-butanol, and methanol were all of glass-distilled chromatographic grade (Burdick and Jackson Laboratories, Inc., Muskegon, Mich.) while 95% ethanol (Warner-Graham Company, Company, Cockeysville, Md.) and glacial acetic acid (J. T. Baker Chemical Company, Phillipsburg, N.J.) were of reagent grade. Among samples, dried sea buckthorn ethanol extract was obtained from China by the courtesy of Professor Tian You Ahang at Beijing Institute of New Technology Application, Beijing, China, and bacitracin was purchased from Sigma Chemical Co., St Louis, Mo.

Example 3: Procedure for Thermostability Test of Solvent Systems

Using the above organic solvents, 11 pairs of solvent systems with a broad spectrum in hydrophobicity were examined for their thermostability. Their compositions are shown in Table 1 below.

TABLE 1

Effects of Temperature on Two-Phase Equilibrium

| | | Effects of Temperature* | | | |
|---|---|---|---|---|---|
| | | Cooling | | Warming | |
| No. | Solvent Systems | UP | LP | UP | LP |
| 1. | Hexane-methanol | + | + | − | − |
| 2. | Hexane-methanol-water (2:1:1) | − | ± | − | − |
| 3. | Hexane-ethyl acetate-methanol-water (1:1:1:1) | ± | + | − | − |
| 4. | Ethyl acetate-water | + | − | − | + |
| 5. | Ethyl acetate-acetic acid-water (4:1:4) | ± | − | − | − |
| 6. | Chloroform-water | − | − | − | − |
| 7. | Chloroform-methanol-water (5:4:3) | + | − | − | − |
| 8. | Chloroform-acetic acid-water (2:2:1) | + | + | − | − |
| 9. | n-Butanol-water | + | − | − | + |
| 10. | n-Butanol-acetic acid-water (4:1:5) | + | − | − | − |

TABLE 1-continued

Effects of Temperature on Two-Phase Equilibrium

| | | Effects of Temperature* | | | |
|---|---|---|---|---|---|
| | | Cooling | | Warming | |
| No. | Solvent Systems | UP | LP | UP | LP |
| 11. | sec.-Butanol-water | − | − | + | + |

*UP: upper phase;
LP: lower phase;
+: development of turbidity;
−: no change in transparency Each solvent mixture, ranging 3–5 ml in volume, was delivered in a test tube (13 mm O.D. and 100 mm in length) and a polyethylene plug was applied to the tube. Then, the content was thoroughly mixed to bring the phase equilibrium at room temperature (about 22° C). The mixing was repeated until two clear layers were obtained.

In the first series of experiments, each tube was immersed in ice water for 5 to 10 seconds to observe turbidity in the upper and/or the lower phases. The second series of experiments was similarly performed with the same set of solvent systems pre-equilibrated at room temperature by immersing each tube into warm water (about 40° C.) for 5 to 10 seconds to observe any development of turbidity in each phase. All experiments were repeated at least twice to ensure the reproducibility of the results.

Example 4: Preparation of Solvent Systems and Sample Solutions

Two different two-phase solvent systems were prepared.
(1) chloroform-methanol-water (4:3:2, v/v/v) for separation of flavonoids from a sea buckthorn ethanol extract; and
(2) chloroform-ethanol-water (%:4:3, v/v/v) for the separation of bacitracin components.

Each solvent mixture was thoroughly equilibrated in a separator funnel at room temperature by repeated vigorous shaking and degassed by opening the stopcork. Two phases separated shortly before use.

The sample solutions of sea buckthorn ethanol extract and bacitracin were prepared in a similar manner by dissolving 50 mg of each sample in 4.5–4.8 ml of the above solvent mixture used for separation.

Example 5: Separation Procedure

In each experiment, the coiled column was first entirely filled with an upper aqueous stationary phase, and the sample solution containing 50 mg of the sample was injected into the head of the column through the sample port. The head-tail relationship of the rotating coil is conventionally defined toward the head of the coil.

The coil planet centrifuge was then rotated at the optimum speed of about 800 rpm, while the mobile phase was pumped into the head of the column at a flow rate of 180 ml/h. The effluent from the outlet of the column was continuously monitored with a Uvicord S spectrophotometer at 254 nm to record the elution curve.

In order to prevent trapping the stationary upper phase with the flow cell, the effluent (lower phase) was passed through the flow cell upwardly. During elution, the fine tube on the flow line between the column outlet and the monitor was immersed in a water bath at a desired temperature which was maintained with a heating rod and a thermal controller (Fisher Scientific Co., Pittsburgh, Penna.).

Example 6: Effect of Solvent Temperature

Phase compositions of the two-phase solvent system used in CCC are in a subtle equilibrium at room temperature. Any change in the ambient temperature may cause one or both phases to change physically, developing a cloudy appearance. If this occurs in the flow cell of the UV-monitor it may produce detrimental effects on the tracing of the elution curve, by means of an intensive noise and/or raised base line.

The effects of cooling and warming on selected 11 pairs of solvent systems are summarized in Table 1 supra. Positive signs indicate a development of turbidity and negative signs indicate no change in transparency.

The results clearly show that in the majority of these solvent systems cooling tends to develop turbidity in the organic phase. That is, that the lower phase in the chloroform systems, both phases in the non-aqueous hexane-methanol system, and the upper phase in the rest of the solvent systems become turbid.

On the other hand, warming provides substantially no change in transparency except for some binary systems including sec-butanol-water, n-butanol-water and ethyl acetate-water.

These results that warming the effluent not only prevents development of the turbidity in the effluent but it may also enable the mobile phase to absorb some amounts of the stationary phase carried over from the separation column. Hence, it serves to maintain high transparency of the effluent passing through the flow cell placed in the UV-monitor.

Example 7: Separation of Flavonoid Compounds Without Improvements of Their Function In the present studies, the above possibility was treated by separation of natural products on two different chloroform solvent systems both utilizing the thermolabile lower non-aqueous phase as the mobile phase.

FIG. 1 shows a typical chromatogram of flavonoids present in a sea buckthorn ethanol extract using a solvent system of chloroform-methanol-water (4:3:2, v/v/v) obtained with a conventional monitoring method for HSCCC.

The effluent was passed upwardly continuously through a straight standard flow cell held vertically in the Uvicord S spectrophotometer where the absorbance was monitored at 254 nm. Because of a thermolabile nature of the lower mobile phase, the UV-tracing of the elution curve was disturbed by an intensive noise and irregular elevation of the base line, thus obscuring a minor peak in the chromatogram.

Example 8: Separation of Flavonoid Compounds in Accordance with the Invention

Figure 2:
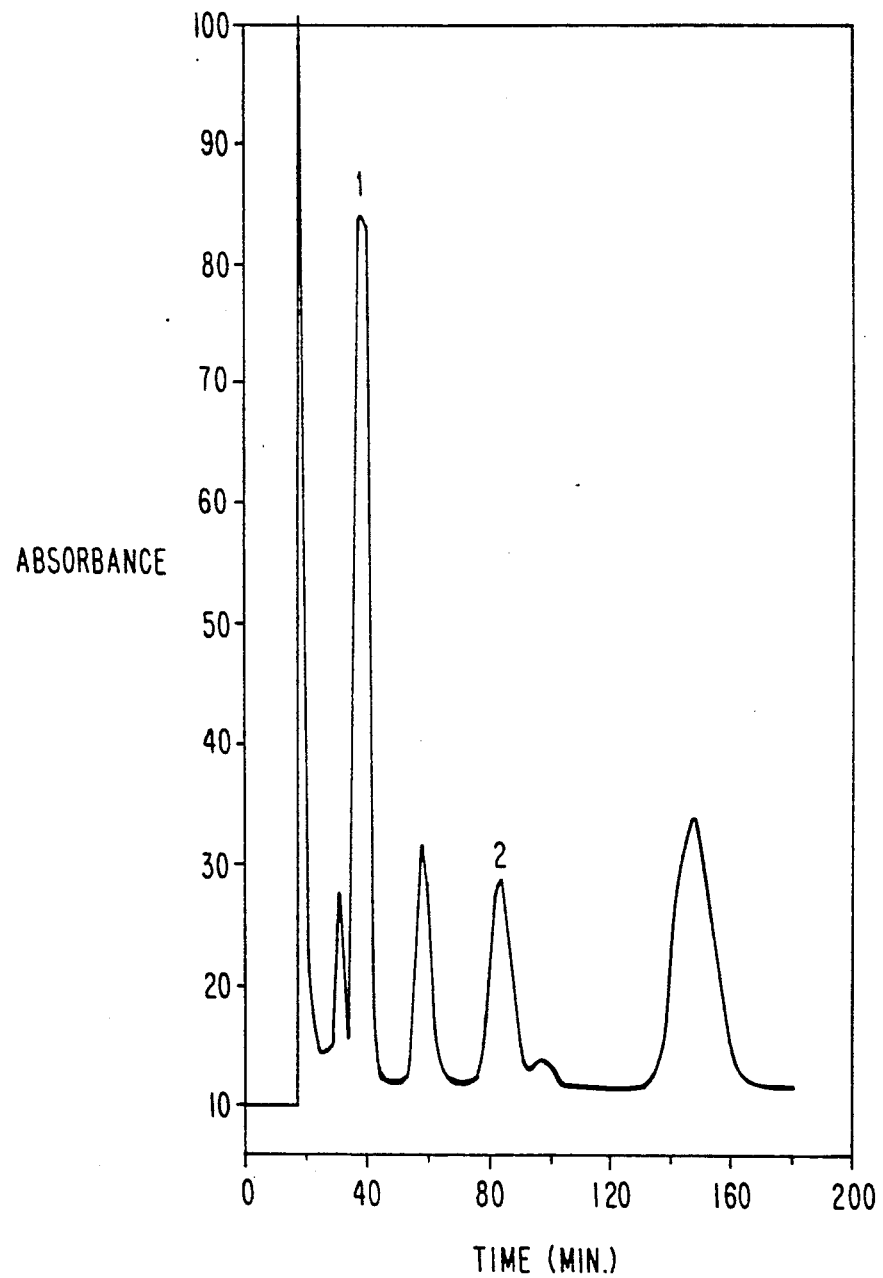
FIG. 2 shows a UV-tracing chart of the separation of flavonoid compounds obtained by heating the effluent obtained in example 8. The effluent from the separation column was passed through a fine tube immersed in a water bath heated at 30° C. Otherwise the experimental conditions were identical to those described in example 7.

FIG. 2 shows a chromatogram obtained under similar experimental conditions, except that the effluent from the separation column was first passed through a narrow tube heated at 30° C. in a water bath before entering the UV-monitor. The results clearly demonstrate a radical improvement in UV-tracing as evidenced by a stable flat base line and smooth tracing of the elution curve. A minor peak, which was obscured by the noise in FIG. 1, was now clearly visible in the chromatogram. A slight thickening of the base line however was found to be caused by periodical passage of gas bubbles through the flow cell.

Example 9: Separation of Flavonoid Compounds in Accordance with the Invention

The formation of gas bubbles in the peripheral portion of the separation column is a common complication in both liquid chromatography and CCC. This undesirable phenomenon can be effectively controlled by applying a narrow-bore tube at the outlet of the monitor. This improvement to the apparatus provides and maintains sufficient back-pressure to substantially eliminate the formation of bubbles.

Figure 3:
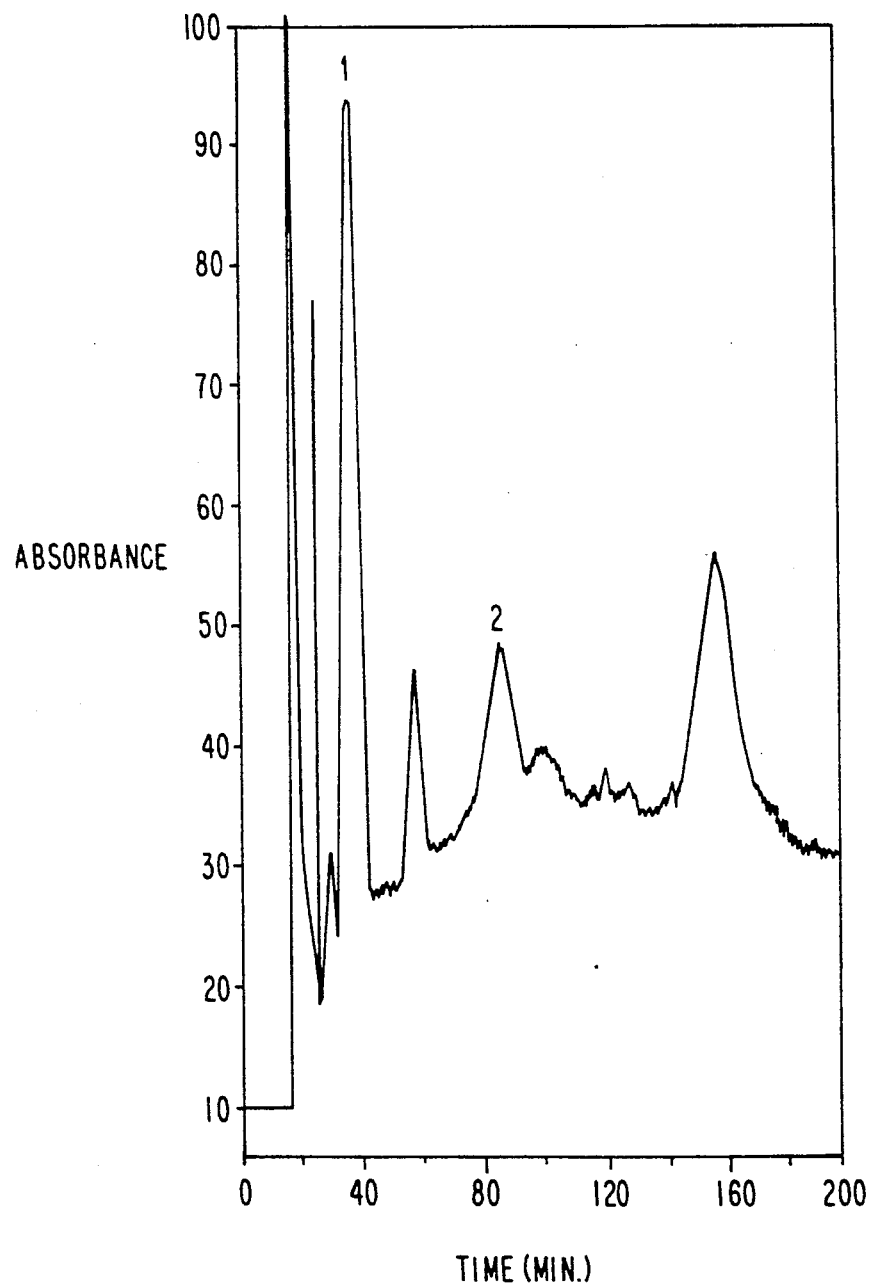
FIG. 3 shows a UV-tracing chart of the separation of flavonoid compounds obtained by applying a fine tube at the outlet of the monitor obtained in example 9. The remaining experimental conditions were as in example 7.

A chromatogram of flavonoids shown in FIG. 3 was obtained from a Uvicord S UV-monitor equipped with a fine tube (0.46 mm I.D. and 3 m in length) at the outlet without heating the effluent. This improvement to the apparatus and the method produced a significant improvement in the tracings over the control run shown in FIG. 1, this improvement substantially eliminated high frequency noise caused by the passage of gas bubbles through the flow cell.

Example 10: Separation of Flavonoid Compounds in Accordance with the Invention Incorporating both Improvements of Examples 8 and 9

The same experiment as in Examples 7-9 was performed by applying the above methods of Examples 8 and 9 combined. In this experiment, the effluent was heated at 30° C. near the inlet of the monitor and a narrow-bore tube was attached at the outlet of the monitor.

Figure 4:
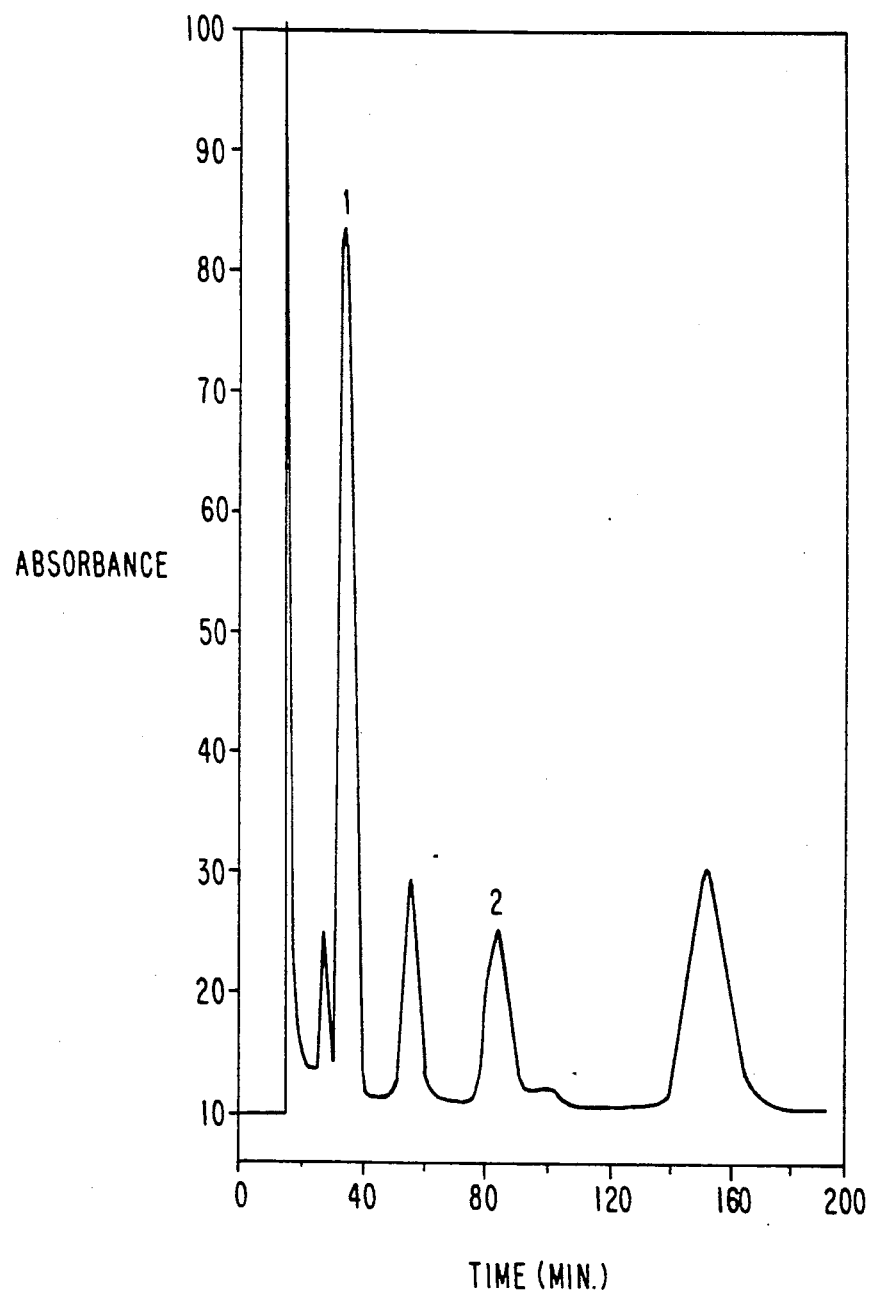
FIG. 4 shows a UV-tracing chart of the separation of flavonoid compounds obtained by the present method as described in example 10. The effluent from the separation column was heated at 30° .C before entering the monitor and a fine tube was applied to the outlet of the monitor to create back pressure.

FIG. 4 shows a countercurrent chromatogram of the flavonoids which was obtained by the present method. The method unexpectedly yielded a noiseless UV-tracing of the elution curve that is comparable in quality to those obtained from HPLC. The chromatogram was found to be substantially identical with an elution curve drawn manually with data obtained from the spectrophotometric analysis of individual fractions without using the present apparatus and method.

Example 11: Separation of Bacitracin in Accordance with the Invention

Figure 5:
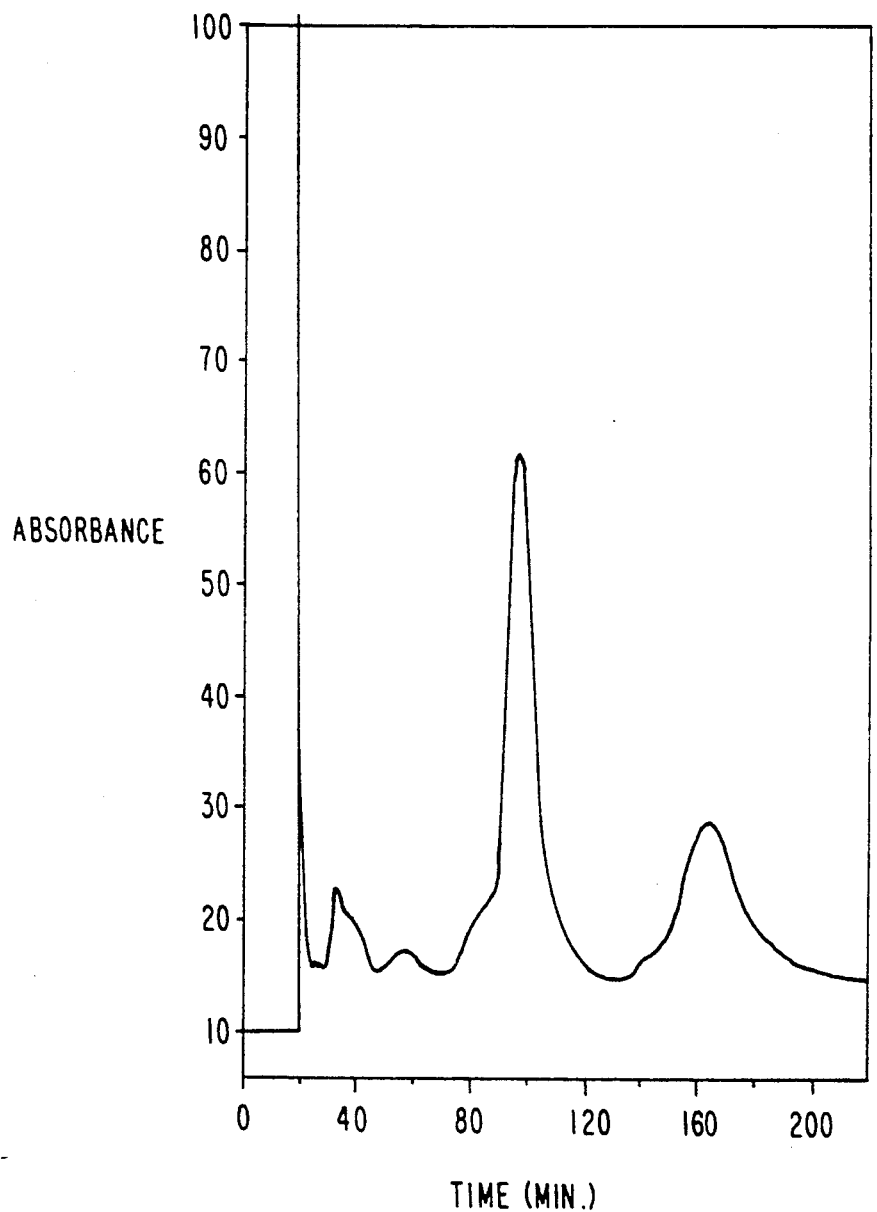
FIG. 5 shows a UV-tracing chart of the separation of bacitracin by the present method as described in example 11. The UV-monitoring conditions were similar to those in example 10.

The method of Example 10 was also successfully applied to the separation of bacitracin with a two-phase solvent system composed of chloroform-ethanol-water (5:4:3, v/v/v) using the lower non-aqueous phase as the mobile phase. The results obtained are shown in FIG. 5.

The invention now being fully described, it will be apparent to one or ordinary skill in the art that many changes and modifications can be made thereto without departing from the spirit or scope of the invention as set forth herein.

We claim:

1. An improved continuous countercurrent chromatography apparatus comprising a separation column provided with first and second ends, feed conduit means for introducing fluids to the first end of the separation column, fluid monitoring means provided with first and second ends, and delivery conduit means connecting the second end of the separation column to the first end of the fluid monitoring means, the improvement comprising
    a thermal regulator means positioned between the delivery conduit means and the monitoring means, said regulator means being capable of maintaining a predetermined temperature;
    means for applying back-pressure to the fluid entering the monitoring means, said back pressure means connected to the first end of the monitoring means; and
    the monitoring means, said back-pressure means connected to the second end of the monitoring means.

2. The continuous countercurrent chromatography apparatus of claim 1 being a high-speed continuous countercurrent chromatography apparatus.

3. The continuous countercurrent chromatography apparatus of claim 1, wherein
    the feed conduit means is provided with a sample port, and fluid pump means connected to the feed conduit means, through the sample port.

4. The continuous countercurrent chromatography apparatus of claim 1, further comprising
    a fraction collector means connected to the outlet of the fluid monitoring means.

5. The continuous countercurrent chromatography apparatus of claim 1, wherein
    the separation column is a helical tube provided with means for rotating about its longitudinal axis.

* * * * *